United States Patent
Uhlmann et al.

(10) Patent No.: US 6,723,706 B2
(45) Date of Patent: *Apr. 20, 2004

(54) MODIFIED ANTISENSE NUCLEOTIDES COMPLEMENTARY TO A SECTION OF THE HUMAN HA-RAS GENE

(75) Inventors: Eugen Uhlmann, Glashütten (DE); Anuschirwan Peyman, Kelkheim (DE); David William Will, Kriftel (DE); Esther Chang, Chevy Chase, MD (US); Kathleen Pirollo, Arlington, VA (US); Antonina Rait, Arlington, VA (US)

(73) Assignee: Aventis Pharma Deutschland GmbH, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,198
(22) PCT Filed: Apr. 30, 1998
(86) PCT No.: PCT/EP98/02546
§ 371 (c)(1),
(2), (4) Date: Feb. 17, 2000
(87) PCT Pub. No.: WO98/50540
PCT Pub. Date: Nov. 12, 1998

(65) Prior Publication Data
US 2003/0064514 A1 Apr. 3, 2003

(30) Foreign Application Priority Data
May 5, 1997 (DE) .......................... 97 107 404

(51) Int. Cl.$^7$ .............. A61K 48/00; C12Q 1/68; C07H 21/04; C07H 21/02; C12P 19/34
(52) U.S. Cl. .............. 514/44; 435/91.1; 435/325; 435/375; 435/6; 536/23.1; 536/24.3; 536/24.31; 536/24.33
(58) Field of Search ............ 435/6, 91.1, 91.3, 435/325, 375; 536/23.1, 23.2, 24.3, 24.33, 24.31, 24.5; 514/44

(56) References Cited

U.S. PATENT DOCUMENTS

| | | | |
|---|---|---|---|
| 5,576,208 A | 11/1996 | Monia et al. | |
| 5,582,972 A | 12/1996 | Lima et al. | |
| 5,582,986 A | 12/1996 | Monia et al. | |
| 5,696,248 A | 12/1997 | Peyman et al. | |

FOREIGN PATENT DOCUMENTS

| | | | |
|---|---|---|---|
| CA | 2087818 | | 7/1993 |
| CA | 2135591 | | 5/1995 |
| WO | 94/08003 | * | 4/1994 |
| WO | WO 94/08625 A | | 4/1994 |

OTHER PUBLICATIONS

Bitonti, A.J., et al., "Regression of Human Breast Tumor Xenografts in Response to (E)–2'–Deoxy–2'– (fluoromethylene)cytidine, an Inhibitor of Ribonucleoside Diphosphate Reductase," Cancer Research, vol. 54, pp. 1485–1490 (1994).

(List continued on next page.)

Primary Examiner—Karen A. Lacourciere
(74) Attorney, Agent, or Firm—Finnegan, Henderson, Farabow, Garrett & Dunner, L.L.P.

(57) ABSTRACT

The invention relates to a specific modified oligonucleotide complementary to a section of the human Ha-ras gene and mRNA, and its use to specifically regulate, modulate or inhibit expression of the HA-ras gene, and its use as a pharmaceutical for the treatment of conditions arising from the abnormal expression of the Ha-Ras gene, in particular in combination with chemotherapy and radiotherapy. The modified oligodeoxynucleotide according to the invention has the sequence 5'-TxAxTxTxCxCxGxTxCxAxT-3'-O—PO$_2$—O—R (SEQ ID NO:1), wherein X is an internucleotide linkage of type o or s, with the proviso that x is an s linkage at least 4 times and at most 9 times, and o means a phosphodiester internucleoside linkage, s means a phosphorothioate internucleoside linkage, R means a C$_8$–C$_{21}$ alkyl group, —(CH$_2$—CH$_2$O)n-(CH$_2$)$_m$—CH$_3$, or —CH$_2$—CH(OH)CH$_2$O—(CH$_2$)$_q$—CH$_3$ wherein n is an integer from 1 to 6, m is an integer from 0 to 20 and q is an integer from 7 to 20 and A is 2'-deoxyadenosine, G is 2'-deoxyguanosine, C is 2'-deoxycytidine and T is thymidine.

30 Claims, 2 Drawing Sheets

Days After First Oligo Injection

Antitumor effects of PPS-C16 in vivo (L+R = control with radiation but without oligonucleotide; I-R = control without radiation and without oligonucleotide; o AS+R = treatment with PPS-C16 (antisense) with radiation;Y AS-R = treatment with PPS-C16 without radiation; 'S+R = treatment with PPS-C16-S (sense) with radiation.)

OTHER PUBLICATIONS

Brown, D., et al., "*Modulation of ras Expression by Antisense, Nonionic Deoxyoligonucleotide Analogs*," Oncogene Research, vol. 4, pp. 243–252 (1989).

Peyman, A., et al., "*Facile Preparation of 3'–derivatized oligodeoxynucleotides*," Bioorganic & Medic. Chemistry Letters, vol. 5, No. 21, pp. 2469–2472 (1995).

Peyman, A., et al., "*Minimally Modified Oligonucleotides of End–Capping and Pyrimidine–Protection*," Biol. Chem. Hoppe–Seyler, vol. 377, pp. 67–70 (1996).

Pirollo, K.F., et al., "*Evidence Supporting a Signal Transduction pathway Leading to the Radiation–Resistant Phenotype in Human Tumor Cells*," Bioch. and Biophys. Res. Comms., vol. 230, pp. 196–201 (1997).

Zon, G., et al., "*Phosphorothioate oligonucleotides*," Eckstein, F., Ed., Oligonucleotides and Analogues, Ch. 4, pp. 87–108 (Oxford Univ. Press, 1991).

* cited by examiner

Antitumor effects of PPS-C16 in vivo (L+R = control with radiation but without oligonucleotide; Ì-R = control without radiation and without oligonucleotide; o AS+R = treatment with PPS-C16 (antisense) with radiation;Ý AS-R = treatment with PPS-C16 without radiation; ¹S+R = treatment with PPS-C16-S (sense) with radiation.)

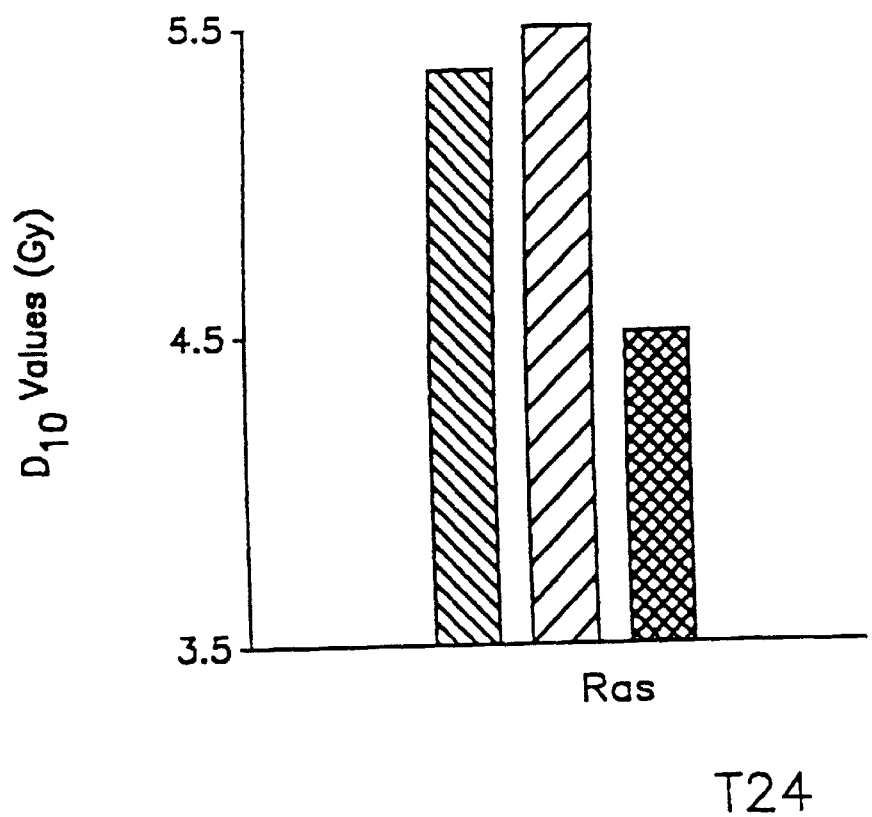
Fig. 2: Reversion of radioresistance in cell culture by treatment with PPS-C16.
($D_{10}$-value: Radiation dose required to reduce survival of cells to 10 %).

SEQUENCE LISTING

<160> NUMBER OF SEQ ID NOS: 5

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 1
tattccgtca t                                                        11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 2
tattccgtca t                                                        11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3
atgacggaat a                                                        11

<210> SEQ ID NO 4
<211> LENGTH: 11
<212> TYPE: DNA

-continued

```
<213> ORGANISM: Artificial Sequence
<220> FEATURE:
<223> OTHER INFORMATION: Description of Artificial Sequence: synthetic
      DNA

<400> SEQUENCE: 4
atgacggaat a                                                              11

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
tattccgtca t                                                              11
```

MODIFIED ANTISENSE NUCLEOTIDES COMPLEMENTARY TO A SECTION OF THE HUMAN HA-RAS GENE

This invention relates to a specific modified oligonucleotide complementary to a section of the human Ha-ras gene and mRNA, and its use to specifically regulate, modulate or inhibit expression of the Ha-ras gene, and its use as a pharmaceutical for the treatment of conditions arising from abnormal expression of the Ha-ras gene.

Antisense oligonucleotides (AO) have proven to be specific inhibitors of gene expression in a large number of systems, both in vivo and in vitro. (Uhlmann and Peyman, Chem. Rev. 1990, 90, 543).

One of the major problems encountered when using unmodified oligonucleotides containing only phosphodiester internucleoside linkages (PO-oligonucleotides) is the rapid degradation of this type of oligonucleotide in cells and biological fluids, such as, for example, serum and cerebrospinal fluid, by a range of nucleolytic activities. A wide range of chemical modifications to oligonucleotides have been carried out in order to improve their nucleolytic stability (Uhlmann and Peyman, Chem. Res. 1990, 90, 543). These modifications include the modification or replacement of the phosphodiester internucleoside linkage, the sugar unit, the nucleobase; or the sugar-phosphate backbone of the oligonucleotides. The most thoroughly investigated type of modification is alteration of the internucleoside linkage, including phosphorothioate (PS), methylphosphonate (MeP) and phosphorodithioate (PSS) linkages. It should be stressed that modification of the oligonucleotide alters not only its nuclease stability but also other characteristics of the oligonucleotide, such as, for example, their cellular uptake, RNaseH activation, and the strength and specificity of binding to their target nucleic acid, and the like. It should be borne in mind that the stability of the modified oligonucleotide in serum, frequently used to determine the nuclease stability of the oligonucleotide, is not the sole determinant of intracellular activity (P. D. Cook in "Antisense Research and Applications", Crooke and Lebleu, Eds., CRC Press, Boca Raton, 1993, Chap.9, p149 et seq.).

The phosphorothioate (PS) modified oligonucleotides are the most widely used type of modified oligonucleotide. The following strategies have been developed for the positioning of PS linkages in antisense oligonucleotides:

(1) Replacement of all phosphodiester internucleoside linkages with phosphorothioate linkages.

The resulting all-phosphorothioate oligonucleotides are much more stable to nucleases than PO-oligonucleotides (Monia et al. J. Biol. Chem. 1996, 271, 14533). For example, degradation of all-PS oligonucleotides by endonucleases is slowed down by a factor of 2–45 relative to a PO oligonucleotide (Stein et al. Nucleic Acids Res. 1988, 16, 3209). In Xenopus oocytes or embryos, the degradation of microinjected PO oligonucleotides proceeds with a half-life of 30 minutes, while all-PS oligonucleotides have a half-life of over 3 hours under the same conditions (Woolf et al. Nucleic Acids Res. 1990, 18, 1763). All-PS oligonucleotides retain their ability to activate RNaseH. The major disadvantages of all-PS oligonucleotides are that their ability to form stable hybrids with their target nucleic acid is reduced, and that they frequently give rise to unspecific "non-antisense" effects (Monia et al., J. Biol. Chem. 1996, 271, 14533).

(2) Oligonucleotides containing both phosphorothioate and phosphodiester internucleoside linkages.

In an effort to overcome the non-antisense effects observed with all-PS oligonucleotides, oligonucleotides containing both phosphorothioate and phosphodiester internucleoside linkages have been synthesized and tested for stability and biological activity.

Ghosh et al. (Anticancer Drug Design 1993, 8, 15) describe a PS—PO oligonucleotide containing various percentages of PS linkages. Their construction follows, for example, the pattern $(PS-PO-PO-PO)_n$, $(PO-PO-PS)_n$, $(PS-PO)_n$, $[(PO)_2-(PS)_2]_n$, $[PO-PS-PS]_n$. They teach that a PS linkage content of at least 50% is required for selective translation inhibition in vitro and that activity drops drastically when the PS content is less than 50%. More recently it has been demonstrated that an oligonucleotide containing 50% PS-linkages arranged in the pattern $(PS-PO)_n$ showed no biological activity in an assay system where an all-PS oligonucleotide and "end-capped" PO—PS oligonucleotides (see below) of the same sequence were highly active (Monia et al., J. Biol. Chem. 1996, 271, 14533).

(3) "End-capped" Oligonucleotides, where one, two or three internucleoside bridges on the 5' and/or the 3' end of the oligonucleotide are phosphorothioate modified. (also known as the "gap technique")

This type of modification is designed primarily to protect the oligonucleotide from degradation by exonucleases. In particular modifications at the 3'-end of the oligonucleotide are desirable as they offer protection from 3'-exonucleases, which are the most abundant nucleases in serum (Uhlmann and Peyman, Chem. Rev. 1990, 90, 543).

An interesting comparison of strategies is found in Hoke et al. (Nucleic Acids Res. 1991, 19, 5743). The authors compare the activity of a range of antisense PS-oligonucleotides against HSV-1 in cell culture. Their findings confirm that 3', or 3'+5', end-capped oligonucleotides (the first three internucleoside linkages being modified in each case), similarly to all-PS oligonucleotides are sufficiently protected against degradation by nucleases in serum. In contrast internally modified (three PS bridges) oligonucleotides and oligonucleotides in which only the 5'-end has been capped (again, the first three internucleoside linkages being modified) are degraded rapidly. In contrast, the authors found that neither 5' nor 3' end capping nor both are sufficient for activity within the cell, and they drew the conclusion that a uniform modification (all-PS) is required to achieve sufficient stability to nucleases in cells.

More recently it has been discovered that pyrimidine nucleosides are the most nuclease susceptible points in oligonucleotides (Peyman, A. and Uhlmann, E., Biol. Chem. Hoppe-Seyler 1996, 377, 67; EP 0 653 439 A2). It was found that a combination of end-capping and PS protection of the pyrimidine positions of oligonucleotides (the so called "minimal modification" approach) is sufficient to make them highly resistant to nuclease degradation. The biological activity (against Herpes simplex virus) of an oligonucleotide with this type of PS modification pattern was comparable to that of an all-PS oligonucleotide.

One of the major problems encountered when using AOs, whether or not they are stabilized against degradation, is their poor cellular uptake. Many approaches have been tried to attempt to ameliorate this problem. Most of these approaches involve the attachment of a variety of substances to the oligonucleotide. Modifications include: the attachment of peptides to oligonucleotides (Lemaitre, M. et al. Proc. Natl. Acad. Sci. USA 1987, 84, 648) and the attachment of lipophilic residues, such as alkyl chains or cholesterol, to oligonucleotides (Saison-Behmoaras, T. et al. EMBO J. 1991, 10, 1111–1118; Will, D. W. and Brown, T. Tetrahedron Lett. 1992, 33, 2729). It has been found, however, that in many cases the introduction of a lipophilic group causes biological effects which are independent of the sequence of the oligonucleotide. Non-specific effects have been reported for cholesterol-oligonucleotide conjugates (Henderson, G. B. and Stein, C. A. Nucleic Acids Res. 1995, 23, 3726.), and for oligonucleotides attached to alkyl chains (Shea, R. G. et al. Nucleic Acids Res. 1990, 18, 3777). Saison-Behmoaras et al (EMBO J. 1991, 10, 1111–1118; WO 96/34008) have reported that a 9mer all-PO oligonucleotide derivatized with a 3'-dodecanol moiety and a 5'-acridine crosslinking agent, and antisense to mutated Ha-ras inhibited T24 human bladder carcinoma cell proliferation. No comparison of the antiproliferative activity of this oligonucleotide with that of the corresponding oligonucleotide without a dodecanol conjugate was made. The cellular uptake of the dodecanol oligonucleotide was reported to be 4 times that of the unmodified oligonucleotide in T24 cells. The acridine-dodecanol modified oligonucleotide had no effect on the proliferation of a human mammary cell line carrying an unmutated Ha-ras gene. This effect can either be attributed to the sequence specificity of the antisense oligonucleotide or to insufficient cellular uptake. Since the uptake of the acridine-dodecanol oligonucleotide was not determined in the human mammary cell line, the effect may be entirely, or at least partly due to the fact that the oligonucleotide was not taken-up by the human mammary cell line, and thus did not have an opportunity to exhibit non-sequence-specific effects on cell proliferation.

About 20% of human tumors have a mutation in one of the three ras genes (Ha-ras, Ki-ras, and N-ras) leading to over-expression of p21 protein which plays an important role in the transformed phenotype (Bos, T. L. 1988 Mutation Res. 1988, 195, 255). It has been reported that inhibition of different ras genes in different cell lines can either have no effect, or inhibit cell proliferation depending on which of the ras genes is controlling the cell proliferation (Chen et al. J. Biol. Chem., 1996, 271, 28259–65). It was suggested that differential modulation of individual ras genes may be an approach to inhibit tumor growth while minimising effects on normal cell growth. One approach to devising successful therapy of Ha-ras-induced tumors is to regulate, modulate or inhibit expression of the Ha-ras gene. Antisense oligodeoxynucleotides (oligonucleotides) have been shown to act as specific inhibitors of ras mRNA expression in cell-free systems, in transformed cells in culture (T. Saison-Behmoaras et al. EMBO J. 1991, 10, 1111–1118; Monia et al. J. Biol. Chem. 1996, 271, 14533), and in ras-activated tumors in vivo (Gray, G. D. et al. Cancer Research, 1973, 53, 577).

In order to modulate the expression of the ras-gene in wild type or in mutated form Brown et al. (Oncogene Res. 1989, 4, 243–252) propose the use of anti-ras oligodeoxy ribonucleoside methylphosphonates which are complementary to the initiation codon region of Balb-ras P21 mRNA (a mouse version of the human Ha-ras Gene). However, it is well known that methyl phosphonates show some major disadvantages compared to phosphorothioates, among other their poor cellular uptake.

Monia et al. (J. Biol. Chem. 267, 19954–19962, 1992; WO 92122651) disclose all-PS antisense oligonucleotides and antisense oligonucleotides containing various percentages of PS linkages (WO 94/08003) directed to the translation initiation site or to codon 12 of the human Ha-ras gene, which however, have the above-mentioned disadvantages concerning the cellular uptake and their poor stability.

Pirollo et al. (Biochem. Biophys. Research Comm. 230, 196–201, 1997) propose the use of anti-ras all-PS oligodeoxynucleotides in order to reverse radio resistance of cancer cells. However, these antisense oligonucleotides show the disadvantages (poor cellular uptake, unstability) as mentioned above.

Therefore, this invention aims to provide an oligonucleotide, modified to improve its stability and cell uptake, complementary to Ha-ras mRNA which specifically regulates, modulates or inhibits expression of the Ha-ras gene in the form of its wild type as well as in its mutated forms, and which can be used to inhibit the proliferation of cancer cells, to reverse radio-resistance in cancer cells, and to treat conditions arising from abnormal expression of the Ha-ras gene.

According to the invention, this problem is solved by providing a modified oligodeoxynucleotide of the sequence SEQ ID NO: 1 5'-TxAxTxTxCxCxGxTxCxAxT-3'-O—$PO_2$—O—R wherein
x is o or s
A is 2'-deoxyadenosine,
G is 2'-deoxyguanosine,
C is 2'-deoxycytidine and
T is thymidine.

The modified oligodeoxynucleotide according to the invention is particularly characterized in that SEQ ID NO:1 has one of the following nucleotide linkage variations:

(a) 5'-TsAsToTcCsCoGoTsCsAsT-3'-O—$PO_2$—O—R,
(b) 5'-TsAsToTcCsCoGsToCsAsT-3'-O—$PO_2$—O—R,
(c) 5'-TsAoTsTcCsCoGoTsCsAsT-3'-O—$PO_2$—O—R,
(d) 5'-TsAoTsTsCsCoGoTsCsAsT-3'-O—$PO_2$—O—R,
(e) 5'-TsAoTsToCsCsGoTsCsAsT-3'-O—$PO_2$—O—R,
(f) 5'-TsAoTsTsCsCsGoTsCsAsT-3'-O—$PO_2$—O—R,
(g) 5'-TsAsToTcCsCsGsToCsAsT-3'-O—$PO_2$—O—R,
(h) 5'-TsAoTsTsCsCsGoTsCsAsT-3'-O—$PO_2$—O—R,
(i) 5'-TsAsTsTsCsCsGoTsCsAsT-3'-O—$PO_2$—O—R,
(j) 5'-TsAsTsToCoCsGoTsCsAsT-3'-O—$PO_2$—O—R,
(k) 5'-TsAsTsToCsCsGsToCsAsT-3'-O—$PO_2$—O—R,
(l) 5'-TsAsTsToCsCoGoTsCsAsT-3'-O—$PO_2$—O—R,
(m) 5'-TsAsToTsCsCoGoTsCsAsT-3'-O—$PO_2$—O—R,
(n) 5'-TsAsToTcCsCsGoTsCoAsT-3'-O—$PO_2$—O—R,
(o) 5'-TsAsToTsCsCoGoTsCoAsT-3'-O—$PO_2$—O—R,
(p) 5'-TsAoTsTsCoCsGoTsCoAsT-3'-O—$PO_2$—O—R,
(q) 5'-TsAsToCsCsGoToCsAsT-3'-O—$PO_2$—O—R,
(r) 5'-TsAsToCoCsGoToCsAsT-3'-O—$PO_2$—O—R,
(s) 5'-ToAoTsToCsCoGoToCsAsT-3'-O—$PO_2$—O—R or
(t) 5'-TsAsTsTsCsCsGoTsCsAsT-3'-O—$PO_2$—O—R, wherein all the variables o, s, R, m, n and q and A, G, C and T have the above-mentioned meanings.

The modified oligonucleotide according to the present invention is complementary to the DNA or RNA deriving from the human Ha-ras gene. The oligonucleotide is complementary to the translation initiation region of Ha-ras mRNA. Therefore it inhibits both wild-type and mutant ras expression resulting in inhibition of tumor cell proliferation. The oligonucleotide is modified to improve its stability and cell uptake characteristics. The oligonucleotide contains four to nine phosphorothioate linkages at certain positions which are especially vulnerable to attack by nucleases. The oligonucleotide is modified at the 3'-end with a $C_8$–$C_{21}$-alkyl or with a $C_1$–$C_{21}$-alkyl, preferably $C_{16}$-alkyl chain, covalently attached through either a phosphodiester bridge, an oligoethyleneglycol phosphodiester linkage, or a glyceryl ether phosphodiester linkage.

A particularly preferred embodiment of the present invention is a modified oligodeoxynucleotide in which SEQ ID NO:1 has the linkage variation of 5'-TsAsToToCsCoGoTsCsAsT-3'-O—PO$_2$—O—R (SEQ ID NO: 1), containing six phosphorothioate linkages, wherein the variables o, s, R, n, m, and q and A, G, C and T have the above-mentioned meanings.

R is particularly preferably —CH$_2$CH(OH)CH$_2$O(CH$_2$)$_{15}$CH$_3$, —(CH$_2$)$_{15}$CH$_3$ or —(CH$_2$CH$_2$O)$_n$—(CH$_2$)$_{15}$CH$_3$, wherein n is an integer from 1 to 6; preferably, n is 1, 2 or 3.

The invention further relates to the preparation of a modified oligonucleotide. Preferably the oligonucleotide is synthesized using standard phosphoramidite chamistry as outlind in examples 1 and 2. Phosphorothioate linkages are for example introduced by sulfurization using the Beaucage reagent.

Surprisingly it was found that particularly the glycerol alkyl ether, i.e. the group —CH$_2$—CH(OH)CH$_2$O—(CH$_2$)$_q$—CH$_3$, q being an integer from 7 to 20, in particular the group —CH$_2$CH(OH)CH$_2$O(CH$_2$)$_{15}$CH$_3$, linked by a phosphodiester linkage to the 3'-end of the oligonucleotide renders an oligonucleotide which no longer depends on the mixing with uptake enhancers for optimal biological activity. This is the first time that an oligonucleotide has been found to exhibit the same biological activity with and without the addition of an uptake enhancer.

The invention further relates to the preparation of a modified oligonucleotide. Preferably the oligonucleotide is synthesized using standard phosphoramidite chemistry as outlined in examples 1 and 2. Phosphorsthioate linkages are for example introduced sulfuization using the Beaucage reagent.

The modified oligodeoxynucleotide according to the present invention as described above is particularly suitable for use as a pharmaceutical. Therefore, a further object of the present invention is the modified olidodeoxynucleotide as described above for use as a pharmaceutical, in particular a pharmaceutical formulation which contains an effective amount of at least one modified oligodeoxynucleotide according to the invention. More particularly, the oligodeoxynucleotide according to the present invention is suitable for preparing a pharmaceutical for the treatment of a disease arising from the overexpression and/or mutation of the Ha-ras gene or diseases arising from a hyperproliferative disorder. Such diseases are in particular cancer, restenosis, or psoriasis.

Transforming activation of ras occurs in approximately 10–20% of human tumors by amplification of the ras gene at the DNA level or by overexpression of the ras protein at the mRNA level. Ras genes can be activated by point mutation at codon 12, 13, or 61 (Barbacid, M. Ann. Rev. Biochem. 1987, 56, 779–827; Bos, supra; Lowy, supra). Point mutation of the Ha-ras gene at codon 12 converts the normally regulated protein to one that is continually active. It is thought that the loss of regulation of normal ras protein function is responsible for the transformation from normal to malignant cell growth.

The modified oligodeoxynucleotide according to the invention is particularly suitable for the regulation, modulation, or inhibition of Ha-ras gene expression. The oligodeoxynucleotide is complementary to the translation initiation region of Ha-ras mRNA. Therefore, it inhibits both wild-type and mutant ras expression resulting in inhibition of tumor cell proliferation. The oligodeoxynucleotide according to the invention is further modified to improve its stability and cell uptake characteristics. The oligodeoxynucleotide contains four to nine, preferably six, phosphorothioate linkages at certain positions which are especially vulnerable to attack by nucleases. The cellular uptake of the oligodeoxynucleotide is further improved by a C$_8$–C$_{21}$-alkyl group or by an C$_1$–C$_{21}$-alkyl group covalently attached through either a phosphodiester bridge, an oligoethyleneglycol phosphodiester linkage, or a glyceryl ether phosphodiester linkage. Due to the improved stability and to the improved cellular uptake the oligodeoxynucleotide according to the present invention depends no longer on the mixing with uptake enhancers and is rendered for optimal biological activity.

Therefore, the oligodeoxynucleotide according to the present invention is particularly suitable for preparing a pharmaceutical which is directed to the regulation modulation or inhibition of Ha-ras gene expression of both, of the Ha-ras wild type gene and its mutants.

In case that the disease resulting from mutation of the Ha-ras gene is cancer, the oligonucleotide according to the invention is particularly suitable for preparing a pharmaceutical which inhibits the proliferation of cancer cells.

However, on the other hand the oligodeoxy nucleotide is advantageously used for preparing a pharmaceutical against cancer which is used in combination with chemotherapy, in particular in cases where the cancer cells have become resistant to chemotherapy, since the oligodeoxynucleotide according to the invention reverses chemoresistance in cancer cells. Therefore, a further object of the present invention is the use of the modified oligodeoxynucleotide as described above for preparing a pharmaceutical which reverses the chemoresistance in cancer cells.

In particular due to this particular effect the oligonucleotide according to the present invention is suitable for preparing a pharmaceutical formulation which contains an effective amount of at least one further chemotherapeutically effective agent. Such chemotherapeutically effective agents are for example cis-platinum and its derivatives, preferably cis-platinum, N-lost derivatives, preferably cyclophosphamide, trofosfamide and ifosfamide, aziridine derivatives, preferably thiothepa, N-nitrosourea derivatives, folic acid antagonists, preferably methotrexate, analogues of purine and pyrimidine bases, preferably 5-fluoro-uracil, cytostatically effective antibiotics, preferably adriamycine, mitomycine and daunorubicine, estrogene antagonists, preferably tamoxifene, and nucleoside derivatives, preferably MDL 101, 731 ((E)-2'-deoxy-2'-(fluoromethylene)cytidine; Cancer Research 54, 1485–1490, 1994).

Ras genes are known to be involved in signal-transduction of various factors for growth, differentiation and oncogenesis. Recent studies have implicated the raf-1 oncogene, which is downstream from ras in the signal transduction pathway, in the expression of the radiation resistance phenotype. It can be shown that the antisense oligonucleotide according to the present invention which is directed to the initiation codon of Ha-ras reverses the radiation resistance level of cancer cells.

Therefore, a further object of the present invention is the use of the modified oligodeoxynucleotide according to the invention for preparing a pharmaceutical for the treatment of cancer in combination with radiotherapy. Particularly, the modified oligodeoxynucleotide according to the present invention is suitable for preparing a pharmaceutical which reverses the radioresistance in cancer cells.

BRIEF DESCRIPTION OF THE DRAWINGS

FIG. 2 shows the reversion of radioresistance in cell culture by treatment with PPS-C16.

Figure 1:
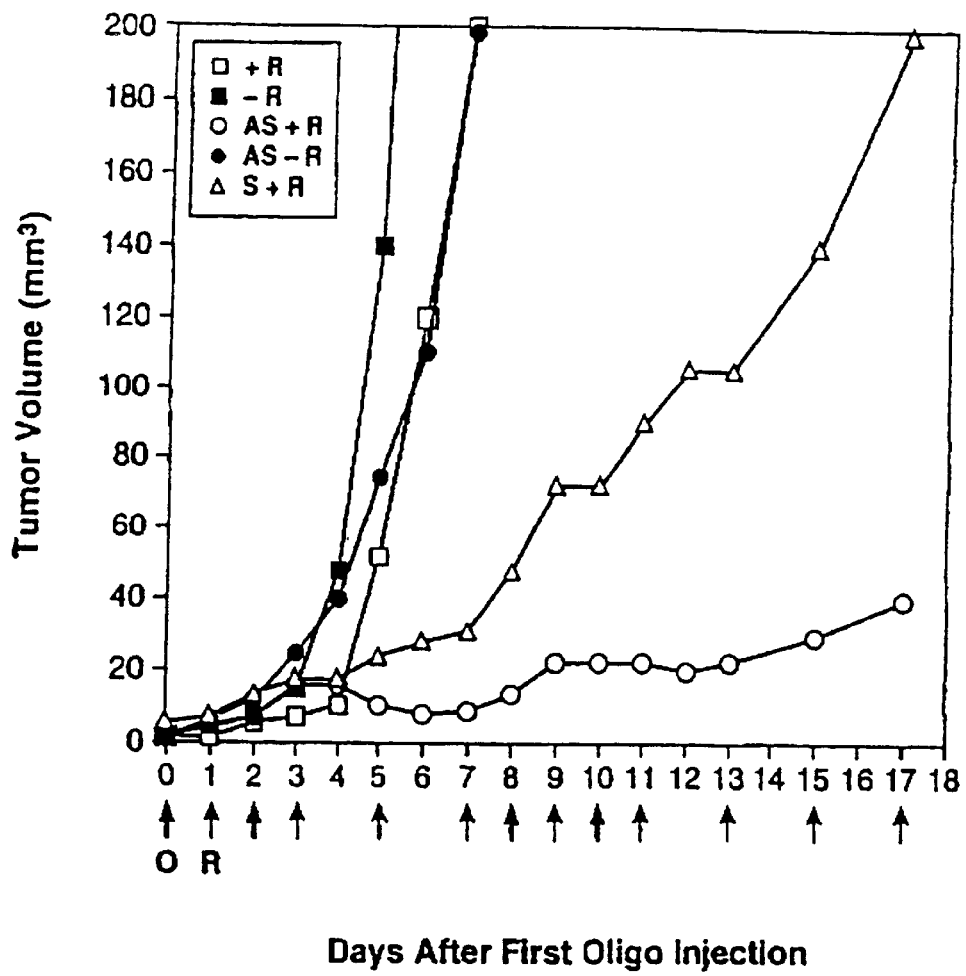
FIG. 1 shows the antitumor effects of PPS-C16 in vivo.

The modified oligonucleotide according to the invention is prepared using an 1-alkanol and oligoethyleneglycol monoalkyl ether, respectively, in conjunction with the 3'-derivatization method described in EP 0 552 767 A2 and EP 0 552 766 A2; or a glyceryl ether phosphodiester linkage, using the solid-support described in Example 1.

EXAMPLES

TABLE 1

List of Oligonucleotides used in Examples.

| Modification | | Code |
|---|---|---|
| Partial Phosphorothioate, Antisense. | SEQ ID NO:1 5'-TsAsToToCsCoGoTsCsAsT-3' | PPS |
| Partial Phosphorothioate, Sense. | SEQ ID NO:2 5'-AsTsGoAoCsGoGoAsAsTsA-3' | PPS-S |
| Partial Phosphorothioate Sense + 3'-C16-alkyl | SEQ ID NO:2 5'-AsTsGoAoCsGoGoAsAsTsA-($PO_2$-O-$CH_2CH(OH)CH_2O(CH_2)_{15}CH_3$)-3' | PPS-C16-S |
| Partial Phosphorothioate Antisense + 3'-C16-alkyl | SEQ ID NO:1 5'-TsAsToToCsCoGoTsCsAsT-($PO_2$-O-$CH_2CH(OH)CH_2O(CH_2)_{15}CH_3$)-3' | PPS-C16 |

Example 1

Synthesis of solid support for the synthesis of oligonucleotides functionalised at the 3'-end with a glycerol hexadecyl ether linked by a phosphodiester linkage.

DL-a-Hexadecylglycerol (1 mmol) was dried by coevaporation with 3×5 ml anhydrous pyridine, then dissolved in anhydrous pyridine (3 ml). The solution was cooled to 0° C. and 4,4'-dimethoxytrityl chloride (1.15 mmol) was added. The reaction was stirred overnight. The reaction was quenched by the addition of water (100 ml) and evaporated to dryness. The residue was taken-up in dichloromethane (20 ml) and extracted 3 times with 10 ml 0.1 M phosphate buffer pH7. The organic phase was dried over sodium sulfate, filtered and evaporated. The residue was dried by coevaporation with 2×5 ml anhydrous pyridine, then dissolved in anhydrous pyridine (2 ml). 4,4-Dimethylaminopyridine (1.4 mmol), and succinic anhydride (2.1 mmol) were added. The reaction was stirred overnight. The reaction solution was evaporated to dryness and coevaporated twice with toluene:dichloromethane/1:1. The residue was taken-up in dichloromethane (20 ml), extracted with 10% citric acid (11 ml) and washed 3 times with water (11 ml). Two drops of triethylamine were added to the organic phase which was then dried over sodium sulfate, filtered and evaporated. The product was purified by silica gel chromatography using a gradient of 1–4% methanol, 1% triethylamine in dichloromethane. The product was obtained as a clear oil in 510 mg (62%) yield. The product (0.056 mmol), N-ethylmorpholine (0.07 mmol) and TBTU (0.056 mmol) were dissolved in DMF (2 ml) and added to aminopropyl controlled-pore glass (CPG; 500 mg; 500Å, Fluka). The mixture was shaken for 4 h and the CPG was filtered-off and washed with methanol and dichloromethane. The CPG was capped for 1 h using acetic anhydride/N-methyl imidazole in THF, filtered and washed with methanol, dichloromethane, THF and diethyl ether. After drying in vacuo the loading of dimethoxytrityl groups was determined to be 80 mmolg$^{-1}$.

Example 2
Oligonucleotide Synthesis

The oligonucleotides were synthesized using an Applied Biosystems 394 DNA synthesizer (Applied Biosystems, Inc., Foster City, USA) and standard phosphoramidite chemistry. After coupling, phosphorothioate linkages were introduced where required by sulfurization using the Beaucage reagent (Iyer et al., 1990) followed by capping with acetic anhydride and N-methylimidazole in tetrahydrofuran. After cleavage from the solid support and final deprotection by treatment with conc. ammonia, the oligonucleotides were purified by gel electrophoresis. For the synthesis of the hexadecyl-modified oligonucleotides the solid support described in Example 1 above was employed. All oligonucleotides were analyzed by negative ion electrospray mass spectroscopy (Fisons Bio-Q) which in all cases confirmed the calculated mass.

Example 3
Inhibition of in vitro Translation of Ha-ras mRNA 0.06 mg RNA was annealed with the appropriate oligonucleotide by heating them together in 10 mM Tris-HCl, pH 7.5, 5 mM $MgCl_2$, 25 mM KCl and 1 mM DTT at 90° C. for 2 minutes and cooling slowly to room temperature. The translation reaction mixture (10 μl) consisted of 0.06 mg of RNA, varying amounts (1, 5, 10 or 20 μM) of oligonucleotide, 8 U of RNasin Ribonuclease Inhibitors (40 U/μl) (Promega Biotec), 20 μM of amino acid mixture minus methionine (Promega Biotec), 0.8 mCi of $^{35}$S-methionine (>1000 mCi/μM, Amersham), 3–6 μl of nuclease-treated Rabbit Reticulocyte Lysate (Promega Biotec), and 1 μM dithiothreitol (DTT). Translation proceeded for 1 hour at 30° C.

After translation, 10 μl of RIPA buffer (PBS, 1% NP40, 0.5% sodium deoxycholeate, 0.1% SDS) with fresh inhibitors (0.1 mg/μl PMSF, 1 mM sodium orthovanadate, 30 ml/μl aprotinin, Sigma, Cat. #A6279) was added to each sample, and the mixture incubated on ice for 20 minutes. 7 μl of 4×SDS sample buffer containing 1.25 M Tris-HCl pH 6.8, 6% SDS, 40% glycerol, 12% 2-mercaptoethanol and 0.001% bromphenol blue was added, and the sample was boiled for 5 minutes. 10 μl of each sample was electrophoresed in a 5–12.5% polyacrylamide gel (PAGE). The completed gel was fixed, dried, and exposed to Kodak XAR-5 film with an intensifying screen at −80° C.
Results:

The claimed antisense oligonucleotide 5'-TsAsTTCsCGTsCsAsT-($PO_2$—O—$CH_2CH(OH)CH_2O$ $(CH_2)_{15}CH_3$)-3' (PPS-C16) (SEQ ID NO:1) inhibited translation of ras p21 protein by approximately 10, 40, 50 and 80% at concentrations of 1, 5, 10, and 20 μM respectively. Controls using the sense oligonucleotide 5'-AsTsGACsGGAsAsTsA-($PO_2$—O—$CH_2CH(OH)CH_2O$ $(CH_2)_{15}CH_3$)-3' (PPS-C16-S) (SEQ ID NO:2) showed no inhibition of translation until 20 μM at which point an 11% inhibition was observed. This strongly suggests that the C16 alkyl chain does not give rise to non-sequence specific effects in this system.

Example 4
Inhibition of p21 Ras Protein Expression in Cell Culture
Cell Lines

NIH3T3 mouse fibroblasts (Chang et al. Biochemistry 30 (1991) 8283–86) transformed by the human Ha-ras (RS485) were used as an experimental cell line to evaluate the sequence-specific inhibition of cell growth and p21 ras protein expression by oligonucleotides directed to the first eleven nucleotides of the initiation codon region of Ha-ras mRNA.

RS485 cells were grown in Dulbecco's Modified Eagle's Medium (DMEM, Flow Labs) supplemented with 10% heat inactivated (30 min. at 65□ C) fetal calf serum (FCS), antibiotics (50 U/μl each of penicillin, streptomycin, and neomycin), and 4 mM of L-glutamine.

Oligonucleotide Treatment of RS485 Cells in Culture

RS485 cells were seeded in 6-well plates (105 cells per well) and, after 20–24 hours (40–60% confluency), were treated with oligonucleotides. Medium was removed from the wells, 1 ml of fresh medium with oligonucleotides at various concentrations was added to each well, and the plates were incubated at 37° C. in an humidified atmosphere containing 5% $CO_2$/95% air for 2448 hours.

Oligonucleotide Lipofection of RS485 Cells in Culture

RS485 cells (40–60% confluency) were transfected with oligonucleotides using Lipofectin™ Reagent and the supplier's protocol (from Life Technologies). Briefly, varying concentrations of oligonucleotides were diluted in 100 μl of serum-free medium. In a separate tube Lipofectin was added to serum-free medium at a concentration of 7 μl/100 μl. After 30 minutes at room temperature, 100 μl of Lipofectin solution was mixed with 100 μl of oligonucleotide solution, incubated for an additional 15 minutes at room temperature, and mixed with 800 μl of serum-free medium. Cells were washed two times with serum-free medium, and the total solution (1 ml) containing the oligonucleotide-Lipofectin complex was overlayed onto the cells. After 6 hours, 1 ml of fresh medium containing 8 mM L-glutamine and 20% calf serum was added, and the cells were incubated for an additional 38 hours. Treated cells were washed with PBS, harvested with trypsin, and cellular proteins were extracted.

Results:

The effect of PPS and PPS—C16 oligonucleotides on p21 expression in RS485 cells was compared in the absence or presence of Lipofectin (supra). After treatment total protein was extracted and p21 levels were determined by Western Blot analysis (infra). Lipofectin alone had no effect on p21 expression. Both the PPS— and PPS—C16-Lipofectin complexes almost completely inhibited p21 expression in RS485 cells at 1 μM concentration. Surprisingly the PPS—C16 oligonucleotide without Lipofectin completely inhibited p21 expression at 5 μM concentration. The PPS oligonucleotide without a C16 modification inhibited p21 expression by only 50% at the same concentration.

A comparison was then made of the effect of PPS-Lipofectin complex and PPS—C16 alone on p21 expression in RS485 cells. The p21 level was decreased by 30% and 43% at 0.25 μM and 0.5 μM PPS-Lipofectin concentrations respectively. Remarkably, the PPS—C16 oligonucleotide without any added Lipofectin showed approximately the same level of inhibition, namely 33% at 0.25 μM and 40% at 0.5 μM. Complete (100%) inhibition of p21 expression was observed at 1 M concentration, indicating that Lipofectin delivery does not augment PPS—C16-mediated inhibition.

Finally, a comparison of the inhibition of p21 expression in RS485 cell by PPS and PPS—C16 in the absence of Lipofectin was made. PPS alone gave an inhibition of approximately 50% at 5 μM. However, at a concentration of only 0.75 μM the PPS—C16 oligonucleotide exhibited nearly 60% inhibition of p21 expression in RS485 cells.

Example 5

Inhibition of Cell Growth and p21 Ras Protein Synthesis in Cell Culture

Cell Growth Inhibition Studies

Cells treated with antisense oligonucleotides, or cells transfected with the oligonucleotide-Lipofectin complexes were harvested and lysed in RIPA buffer. Total protein levels in each well were determined spectrophotometrically. Inhibition of cell growth was estimated as the ratio of protein (mg) in the oligonucleotide-treated cells compared with that in the control. The control was either protein from cells treated with Lipofectin only, or protein from untreated cells.

Western Blot Analysis of Ras Protein

Total cellular protein was prepared by lysing cells in RIPA buffer with freshly added inhibitors (PMSF, aprotinin, sodium orthovanadate) and homogenizing through 21-gauge needles according to the protocol provided by Santa Cruz Biotechnology, Inc. The extracts were cleaned by centrifugation at 15,000×g for 20 min at 4° C. and the protein concentration of the supernatant was determined. 40 μg of protein was size fractionated in 5–12.5% PAGE and electroblotted onto a nitrocellulose membrane. The membrane was incubated with primary antibody against Ha-Ras (C-20) (Santa Cruz Biotechnology, Inc.) and then with Horseradish Peroxidase-conjugated goat anti-rabbit immunoglobulin G. The ECL chemo-luminescent Western system (Amersham, Arlington Heights, Ill.) was used to detect secondary probes.

Results:

A series of experiments were performed to study the sequence—sequence toxic effect of the PPS and PPS—C16 oligonucleotides on RS485 cells shows that treatment of RS485 cells with 1–5 μM of PPS and PPS—C16 in the presence of Lipofectin (supra) reduces cell growth by approximately 35–50% over a 2 day period. Lipofectin alone has a slight toxic effect (ca. 15%) on cells. Comparison of the Western blot analysis of p21 expression inside RS485 cells (supra) with the cell growth inhibition by PPS and PPS—C16 demonstrates that a 1 μM oligonucleotide/Lipofectin complex concentration totally inhibits p21 expression, but inhibits cell growth by only 35%.

PPS—C16 without Lipofectin inhibits cell growth by 11% at 0.75 μM while inhibiting p21 expression by 60% (supra). PPS inhibits cell growth by 22% at a concentration of 5 μM, a concentration at which it inhibits p21 expression by 50%. Lipofectin exerts a toxic effect when used with PPS at concentrations higher than 1 μM and that the PPS—C16 oligonucleotide without Lipofectin is, in the concentration range 0.25–1 μM, just as effective as the PPS oligonucleotide with Lipofectin.

Example 6

Reversal of Radioresistance—Animal Study

Antitumor Effects of Antisense Oligonucleotides in vivo

RS504 cells are NIH 3T3 cells transformed by the Ha-ras oncogene isolated from EJ/T24, a human bladder carcinoma. Tumor were induced by injecting 5×10⁶ RS504 cells subcutaneous in female athymic NCr-nu mice. Forty-eight hours later, when tumors were evident (~6 mm³), partially phosphorothioated C16-modified [PPS—C16] antisense [AS] or sense [S] oligonucleotides were injected directly into the tumors at a concentration of 50 μl of 5 μM solution (250 pmol) per tumor. After 24 hours, tumors were irradiated with a 2.0 Gy dose (thin arrows, see FIG. 1). Irradiation was repeated every 48 hours until an accumulated dose of 20 Gy had been delivered. Oligonucleotide injections were repeated at 48 hours [50 μl], 192 hours [50 μl], and 240 hours [100 μl] following the initial injection (bold arrows, see FIG. 1). Tumor volume was recorded in mm³. Controls consisted of tumors that were not injected with oligonucleotides and not irradiated, tumors that were not injected with oligonucleotides but were irradiated; and tumors injected with antisense PPS—C16 oligonucleotides but not irradiated.

Tumor Growth

Ras genes are known to be involved in signal-transduction of various factors for growth, differentiation and oncogenesis. Recent studies have implicated the raf-1 oncogene, which is downstream from ras in the signal transduction pathway, in the expression of the radiation resistence phenotype. It can be shown that the antisense oligonucleotide according to the invention reverses the radiation resistance level of the cells. To determine if there were differences in the effects of radiation on ras-induced tumors following treatment with oligonucleotides, RS 504-induced tumors in nude mice were treated with antisense and sense PPS—C16 oligonucleotides. FIG. 1 shows that antisense PPS—C16 oligonucleotide treatment in conjunction with radiation was most effective in inhibiting tumor growth during the 17 days of observation and treatment.

Example 7
Reversion of Radioresistance in Cell Culture

Reversion of radioresistance phenotype in cell culture by treatment with PPS—C16 Bladder (T24) carcinoma cell lines (obtained from ATCC, Rockville, Md.) were maintained in McCoy's 5A medium supplemented with 10% fetal bovine serum 50 µg/ml each of penicillin, streptomycin anfd neomycin and 2 mM L-glutamine.

For oligonucleotide treatment, the cells were plated at $1\times10^5$ cells/well in 6-well tissue culture plates. Twenty-four hours later, at approximately 40–60% confluency, the cells were transfected with oligonucleotides, facilitated by Lipofectin Reagent, using essentially the protocol supplied by the manufacturer, Life Technologies, Inc. After 6 hours, the lipofection solution was removed and the monolayer washed with fresh medium containing 8 mM L-glutamine and 20% serum. The cells were then incubated for an additional 16–18 hours in 1 ml of this medium. Cellular response to radiation was evaluated by the colony survival assay. Exponentially growing monolayer cultures of each cell line were treated with the oligonucleotides as described above the cells were harvested 24–48 hours later, suspended in fresh medium and irradiated at room temperature with graded doses of $^{137}Cs$ γ rays at a dose of approximately 36 Gylminute in a J. L. Shephard and Associates Mark I irradiator. Afterward, the cells were diluted and plated at a concentration of 300 to 5000 cells per well in a 6-well tissue culture plate. Two to three days after plating, the cells were supplemented with 0,5 ml of serum plus 5 µg/ml hydrocortisone. Approximately 7–14 days later, the cells were stained with 1% crystal violet and colonies (comprising 50 or more cells of normal appearance) were scored. The $D_{10}$-value (radiation dose required to reduce survival of cells to 10%) for antisense-treated (PPS—C16) T24 cells drops from the highly resistant level of 5.5 (untreated or sense-treated PPS—C16—S) to 4.5 Gy, a value dose to what is considered to be radiosensitive. These results are shown in FIG. 2.

What is claimed is:

1. A modified oligodeoxynucleotide comprising SEQ ID NO:1, wherein the modified oligodeoxynucleotide is characterized in that SEQ ID NO:1 has one of the following nucleotide linkage variations;

(a) 5'-TsAsToToCsCoGoTsCsAsT-3'O—PO$_2$—O—R,
(b) 5'-TsAsToToCsCoGsToCsAsT-3'O—PO$_2$—O—R,
(c) 5'-TsAoTsToCsCoGoTsCsAsT-3'O—PO$_2$—O—R,
(d) 5'-TsAoTsTsCsCoGoTsCsAsT-3'O—PO$_2$—O—R,
(e) 5'-TsAoTsToCsCsGoTsCsAsT-3'O—PO$_2$—O—R,
(f) 5'-TsAoTsTsCsCsGoTsCsAsT-3'O—PO$_2$—O—R,
(g) 5'-TsAsToToCsCsGsToCsAsT-3'O—PO$_2$—O—R,
(h) 5'-TsAoTsTsCsCsGoTsCsAsT-3'O—PO$_2$—O—R,
(i) 5'-TsAsTsTsCsCsGoTsCsAsT-3'O—PO$_2$—O—R,
(j) 5'-TsAsToToCoCsGoTsCsAsT-3'O—PO$_2$—O—R,
(k) 5'-TsAsTsToCsCsGoTsCsAsT-3'O—PO$_2$—O—R,
(l) 5'-TsAsTsToCsCoGoTsCsAsT-3'O—PO$_2$—O—R,
(m) 5'-TsAsToTsCsCoGoTsCsAsT-3'O—PO$_2$—O—R,
(n) 5'-TsAsToToCsCsGoTsCoAsT-3'O—PO$_2$—O—R,
(o) 5'-TsAsToTsCsCoGoTsCoAsT-3'O—PO$_2$—O—R,
(p) 5'-TsAoTsTsCoCsGoTsCoAsT-3'O—PO$_2$—O—R,
(q) 5'-TsAsTsToCsCsGoTsCsAsT-3'O—PO$_2$—O—R,
(r) 5'-TsAsTsToCoCsGoToCsAsT-3'O—PO$_2$—O—R,
(s) 5'-ToAoTsToCsCoGoToCsAsT-3'O—PO$_2$—O—R,
(t) 5'-TsAsTsTsCsCsGoTsCsAsT-3'O—PO$_2$—O—R, wherein:
o means a phosphodiester internucleoside linkage,
s means a phosphorothioate internucleoside linkage,
R means a $C_8$-$C_{21}$ alkyl group, —(CH$_2$—CH$_2$O)$_n$—(CH$_2$)$_m$—CH$_3$ or —CH$_2$CH(OH)CH$_2$O(CH$_2$)$_q$—CH$_3$, wherein n is an integer from 1 to 6, m is an integer from 0 to 20 and q is an integer from 7 to 20 and
A is 2'-deoxyadenosine,
G is 2'-deoxyguanosine,
C is 2'-deoxycytidine and
T is thymidine.

2. The modified oligodeoxynucleotide as claimed in claim 1, having the sequence:

5'-TsAsToToCsCoGoTsCsAsT-3'-O—PO$_2$—O—R (SEQ ID NO: 1)

wherein
o means a phosphodiester internucleoside linkage,
s means a phosphorothioate internucleoside linkage,
R means a $C_8$-$O_{21}$ alkyl group, (CH$_2$CH$_2$O)$_n$(CH$_2$)$_m$CH$_3$ or CH$_2$CH(OH)CH$_2$O—(CH$_2$)$_q$—CH$_3$ wherein n is an integer from 1 to 6,
m is an integer from 0 to 20 and q is an integer from 7 to 20 and
A is 2'-deoxyadenosine,
G is 2'-deoxyguanosine
C is 2' deoxycytidine
T is thymidine.

3. The modified oligodeoxynucleotide as claimed in claim 1 wherein R is —CH$_2$CH(OH)CH$_2$O(CH$_2$)$_{15}$OH$_3$.

4. The modified oligodeoxynucleotide as claimed in claim 1 wherein R is —(CH$_2$)$_{15}$OH$_3$.

5. The modified oligodeoxynucleotide as claimed in claim 1 wherein R is —(CH$_2$CH$_2$O)$_n$—(CH$_2$)$_{15}$CH$_3$ and n is an integer from 1 to 6.

6. The modified oligodeoxynucleotide as claimed in claim 5 wherein n is 1.

7. The modified oligodeoxynucleotide as claimed in claim 5 wherein n is 2.

8. The modified oligodeoxynucleotide as claimed in claim 5 wherein n is 3.

9. A pharmaceutical formulation which contains an effective amount of at least one modified oligodeoxynucleotide as claimed in claim 1, and a pharmacologically acceptable carrier.

10. The pharmaceutical formulation as claimed in claim 9, further comprising an effective amount of at least one chemotherapeutically effective agent.

11. The pharmaceutical formulation as claimed in claim 10 wherein at least one agent is cis-platinum.

12. The pharmaceutical formulation as claimed in claim 10 wherein at least one agent is N-lost.

13. The pharmaceutical formulation as claimed in claim 12 wherein at least one agent is cyclophosphamide.

14. The pharmaceutical formulation as claimed in claim 12 wherein at least one agent is trofosfamide.

15. The pharmaceutical formulation as claimed in claim 12 wherein at least one agent is ifosfamide.

16. The pharmaceutical formulation as claimed in claim 10 wherein at least one agent is aziridine.

17. The pharmaceutical formulation as claimed in claim 16 wherein at least one agent is thiothepa.

18. The pharmaceutical formulation as claimed in claim 10 wherein at least one agent is N-nitroso-urea.

19. The pharmaceutical formulation as claimed in claim 10 wherein at least one agent is a folic acid antagonist.

20. The pharmaceutical formulation as claimed in claim 19 wherein at least one agent is methotrexate.

21. The pharmaceutical formulation as claimed in claim 10 wherein at least one agent is an analog of a purine or pyrimidine base.

22. The pharmaceutical formulation as claimed in claim 21 wherein at least one agent is 5-fluoro-uracil.

23. The pharmaceutical formulation as claimed in claim 10 wherein at least one agent is a cytostatically effective antibiotic.

24. The pharmaceutical formulation as claimed in claim 23 wherein at least one agent is adriamycine.

25. The pharmaceutical formulation as claimed in claim 23 wherein at least one agent is mitomycine.

26. The pharmaceutical formulation as claimed in claim 23 wherein at least one agent is daunorubicine.

27. The pharmaceutical formulation as claimed in claim 23 wherein at least one agent is an estrogen antagonist.

28. The pharmaceutical formulation as claimed in claim 10 wherein at least one agent is tamoxifene.

29. The pharmaceutical formulation as claimed in claim 10 wherein at least one agent is a nucleoside.

30. The pharmaceutical formulation as claimed in claim 29 wherein at least one agent is MDL 101,731.

* * * * *